United States Patent [19]

Raines et al.

[11] 4,014,797
[45] Mar. 29, 1977

[54] INTRAVENOUS INJECTION APPARATUS AND NEEDLE ADAPTER WITH FILTER AND METHOD OF MAKING SAME

[75] Inventors: Kenneth Raines; George K. Burke, both of Bethlehem, Pa.

[73] Assignee: Burron Medical Products, Inc., Bethlehem, Pa.

[22] Filed: May 20, 1975

[21] Appl. No.: 579,199

Related U.S. Application Data

[60] Division of Ser. No. 423,682, Dec. 11, 1973, Pat. No. 3,970,084, which is a continuation-in-part of Ser. No. 299,268, Oct. 20, 1972, abandoned.

[52] U.S. Cl. .......................... 210/446; 128/214 R; 210/451; 210/457; 210/496; 210/DIG. 23
[51] Int. Cl.² .......................................... C02C 1/14
[58] Field of Search ........ 128/221, 218 N, 214 RC, 128/214.2; 210/446, 448, 451, 452, 457, 496, DIG. 23, 466

[56] References Cited

UNITED STATES PATENTS

| 3,242,029 | 3/1966 | Deans ................................. 128/221 |
| 3,322,114 | 5/1967 | Portnoy et al. ................ 128/214 R |
| 3,469,581 | 9/1969 | Burke ................. 128/221 |
| 3,722,697 | 3/1973 | Burke ................. 210/451 |
| 3,756,235 | 9/1973 | Burke ................. 128/221 |
| 3,817,389 | 6/1974 | Weichselbaum ............... 128/214 C |
| 3,882,026 | 5/1975 | McPhee ............................. 210/446 |
| 3,903,887 | 9/1975 | Antoshkiw ......................... 128/221 |
| 3,933,652 | 1/1976 | Weichselbaum .................. 210/446 |

Primary Examiner—Frank W. Lutter
Assistant Examiner—Frank Sever
Attorney, Agent, or Firm—Shoemaker and Mattare, Ltd.

[57] ABSTRACT

An intravenous injection apparatus comprising at least a pair of filters serially arranged between opposite ends of an intravenous injection set, and a needle adapter and filter and method of making same, wherein the adapter includes a housing having a bore therethrough and an insert positioned within said bore, said insert having a bore therethrough and a unique filter presealed to said insert across the bore through the insert to filter contaminants from material flowing through said needle adapter.

6 Claims, 10 Drawing Figures

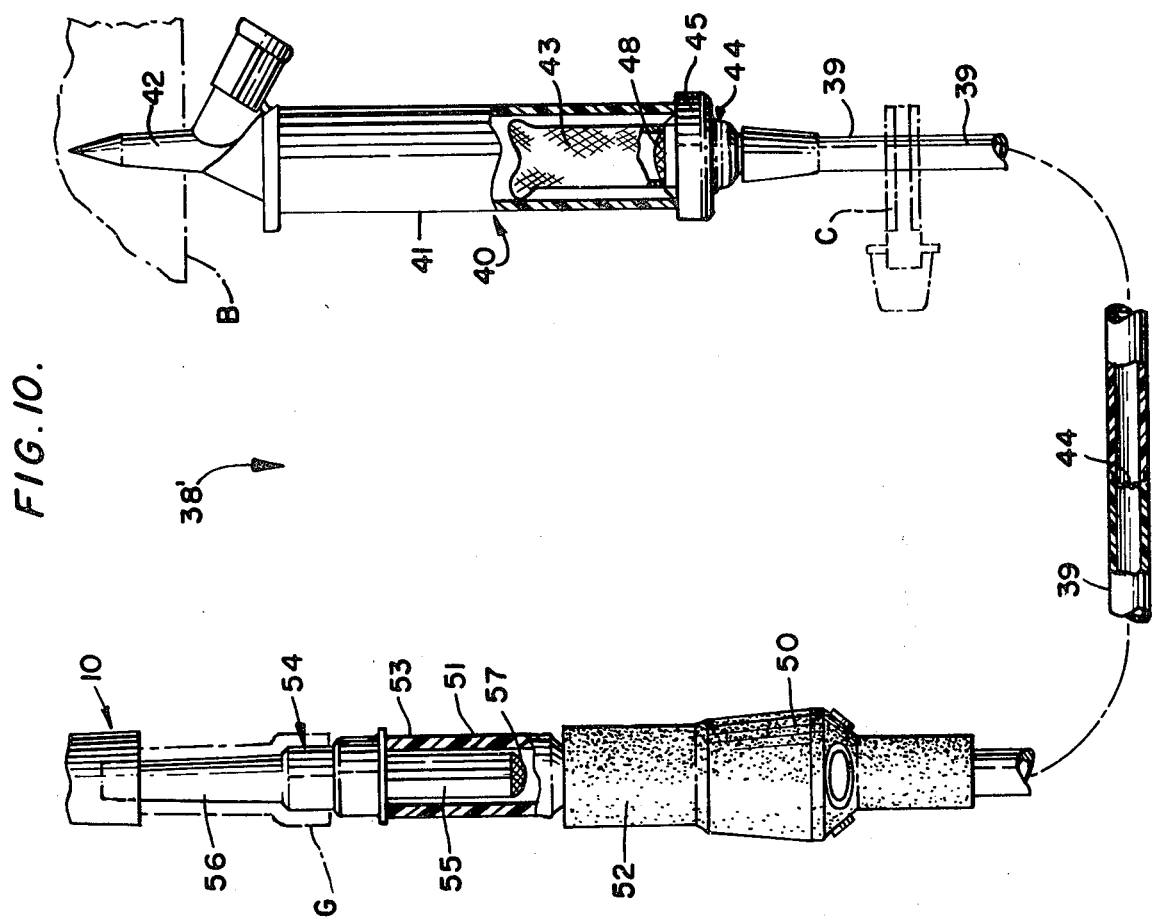
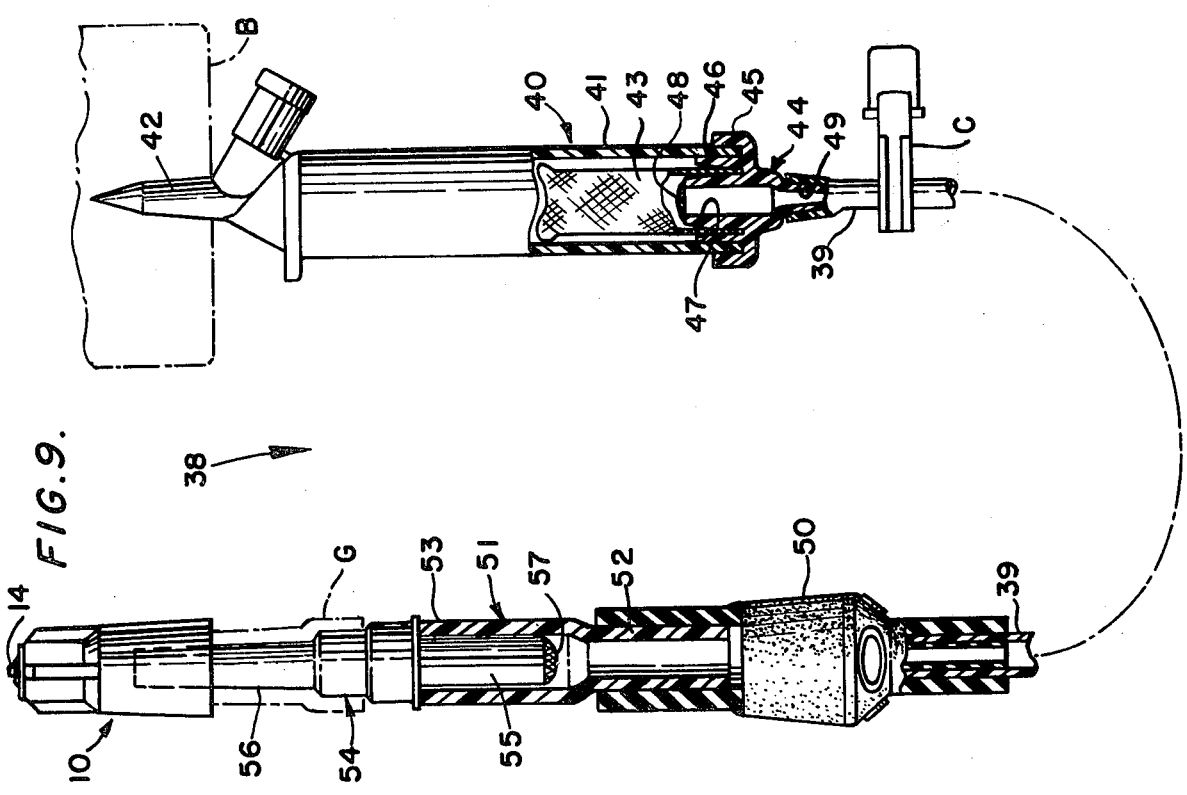

INTRAVENOUS INJECTION APPARATUS AND NEEDLE ADAPTER WITH FILTER AND METHOD OF MAKING SAME

This application is a division of application Ser. No. 423,682, filed Dec. 11, 1973, Now U.S. Pat. No. 3,970,084, which is a continuation-in-part of application Ser. No. 299,268, filed Oct. 20, 1972, now abandoned.

BACKGROUND OF THE INVENTION

In the treatment of various illnesses and diseases, many different types of solutions or medicaments are injected into the veins of patients. Many devices are provided in the prior art for handling such solutions and medicaments and for injecting the solutions and medicaments into the veins of a patient. During the preparation, handling and injection of such solutions and medicaments into the veins of a patient, contaminants are frequently introduced into the solutions or medicaments. Some examples of contaminants are small pieces or particles of flash which break off of the injection apparatus, or pieces of stoppers or vials or cartridges which are punctured or broken in the preparation of a solution of medicament for injection into the vein of a patient. These contaminants must be removed prior to injection of the solutions or medicaments into the veins of a patient, and various filtration devices are known in the prior art for removing these contaminants. For example, specially shaped screen type filter discs have been employed in the prior art to obtain maximum filtration area, but such screen type filter discs are relatively expensive to make and are difficult to assemble. Further, it is difficult to place such filter discs in intravenous apparatus in such a manner that the construction is leakproof, with all flow occurring through the filter disc. In some instances with prior art filters, the solution or medicament seeps around the filter disc and thus all of the contaminants in the solution or medicament are not removed.

Another filter used in the prior art is commonly referred to as a depth filter. A depth filter consists of fibers, particles or fragments of materials of some type pressed or bended together to form a tortuous maze or flow passage. The pores of a depth filter can be made course or fine or variable in size. Initially, such filters have a high flow rats and contaminants are entrapped throughout the matrix of the filter, with contaminate particles working their way through the filter until they are trapped therein. Such filters are highly susceptible to clogging with a resultant increase in the operating pressure or pressure differential therecross and some of the contaminants may eventually work their way through the filter.

With the present invention, a simple and unique construction is provided wherein a screen type filter disc is sealed to an insert and the insert and filter are then positioned within a needle adapter across a bore therethrough to filter contaminants from a solution or medicament passed through the adapter. The filter disc according to the present invention is sealed to the insert so that there is no possibility of the solution or medicament leaking or seeping around the filter. In a preferred form of the invention, the filter is dome shaped, with the dome shape being automatically achieved when the filter is secured to the insert; and accordingly, the filter disc of the present invention is substantially more economical, is easier to assemble, and is more efficient than prior art filters.

Still further, it is difficult to achieve a constant flow rate in conventional IV sets as the source of liquid to which the IV set is connected becomes depleted. For example, when an IV set is connected to a bag containing a liquid to be administered to a patient or to be mixed with another material or the like, the initial pressure, and thus the flow rate through the device is relatively high due to the available head pressure of the liquid. However, as the liquid in the bag is depleted, the head pressure is reduced and thus the flow rate decreases. The change in flow rate or drip rate (drops per minute) from initial flow to final flow in such a system can typically vary approximately 771 percent over a three hour period. A change in drip rate or flow rate of this magnitude is clearly critical and some means of controlling the rate must be provided. In the prior art, various devices, such as clamps and the like, are used to regulate the flow rate, but such devices require constant attention and frequent adjustment to insure that the proper flow rate is obtained, thus requiring the attention of a nurse or other person.

The present invention provides at least a pair of filters in the IV set, with the filters serially arranged, preferably one at or near the inlet end of a length of IV tubing, as for example, near or in a drip chamber, and another at or near the outlet end of the length of tubing, as for example in a filter adapter and needle assembly. The pair of filters thus provided, surprisingly results in a nearly constant flow rate through the IV set during the time it takes to deplete the liquid in the bag.

OBJECTS OF THE INVENTION

It is an object of this invention to provide a unique and simple needle adapter and filter and method of making same, wherein the adapter includes a housing having a bore therethrough with an insert secured within the bore. A screen type filter disc is secured and sealed to the insert prior to positioning of the insert in the bore, for filtering contaminants and particulate matter from materials or solutions flowing through the bore. The dome shaped configuration of the filter disc is automatically achieved when the filter is secured to the insert, and thus results in a much more economical and efficient filter than exists in the prior art.

Another object of the invention is to provide an intravenous injection assembly wherein at least two serially arranged filters are provided in an IV set to maintain the flow rate through the IV set substantially at a preset, constant flow rate.

BRIEF DESCRIPTION OF THE DRAWINGS

FIG. 4a is a view in section of a slightly modified filter disc and insert for the hub of FIG. 1.

FIG. 5 illustrates the insert prior to attachment of the filter disc thereto.

FIG. 6 shows a web of filter material being pressed against an end of the insert.

FIG. 7 shows the insert and web separated, with a filter disc cut from the web and sealed to the insert.

FIG. 8 illustrates the manner in which the dome shaped configuration of the filter disc is achieved during attachment of the filter disc to the insert.

FIG. 9 is an enlarged view, with parts broken away and parts shown in section, of a dual filter intravenous assembly.

FIG. 10 is a view similar to FIG. 9 of a slightly modified form of the invention, with a third filter in the tubing between the ends thereof.

DETAILED DESCRIPTION OF THE INVENTION

Figure 1:
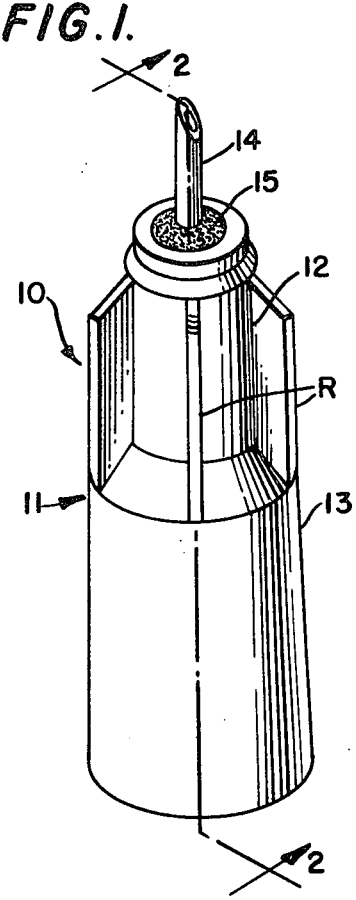
FIG. 1 is a top perspective view of a needle adapter according to the present invention.

In the drawings, wherein like reference numerals indicate like parts throughout the several views, a tubular needle adapter or hub is indicated generally at 10 in FIG. 1. The adapter comprises a housing 11 having an upper portion 12 with a plurality of circumferentially spaced ribs R thereon and a diametrically enlarged lower portion 13. An IV needle 14 or section of PVC tubing or the like is secured in the upper end of the upper portion 12 with an epoxy adhesive 15 or the like.

Figure 2:
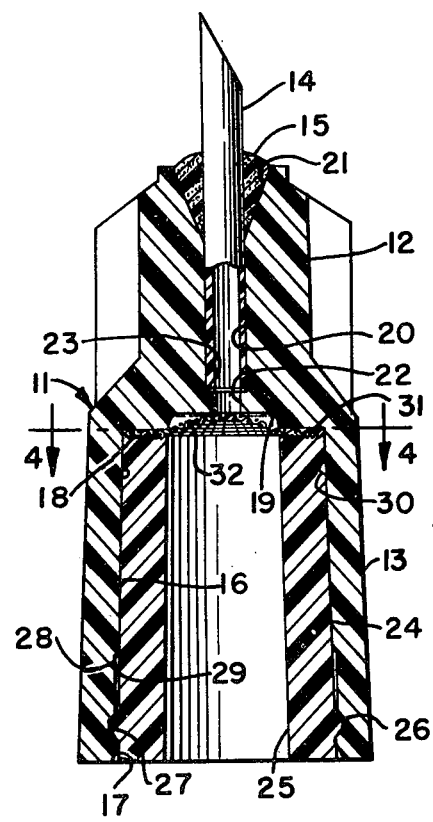
FIG. 2 is a sectional view taken along line 2—2 in FIG. 1.
Figure 3:
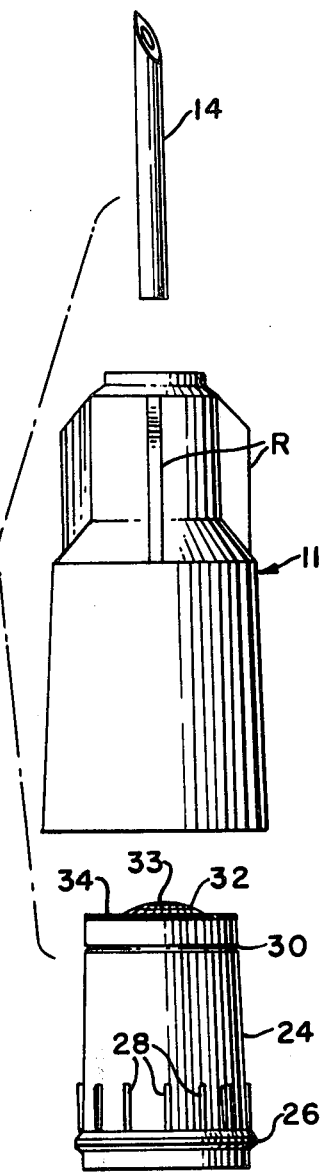
FIG. 3 is an exploded view in elevation of the housing, insert and IV needle of the present invention.

In FIG. 2, the lower portion 13 of housing 11 has a bore or chamber 16 therein extending from an open end 17 of the housing to an axially downwardly facing shoulder 18 approximately medially of the opposite ends of the housing 11. A shatlow cavity or chamber 19 is formed in the housing 11 radially inwardly of shoulder 18 and extends in the housing toward the upper portion 12 thereof. A bore 20 extends from the chamber 19 through housing portion 12 and is conically outwardly flared or enlarged at 21 at the upper end of portion 12 to define a chamber or recess for receiving the epoxy adhesive 15. The lower end of bore 20 is diametrically reduced at 22 to define a radially inwardly extending axially upwardly facing shoulder 23. The IV needle 14, or PVC tubing or the like, is snugly fitted within bore 20, and the lower end thereof rests against shoulder 23. The epoxy adhesive 15 surrounds the needle 14 in the recess 21 to securely adhesively bond the needle to the housing 11.

A substantially tubular or cylindrical insert 24 is fitted within the bore or chamber 16 of housing 11 and has an axial bore 25 therethrough of substantially the same diameter as the diameter of chamber 19 in the housing 11. The length of insert 24 is substantially the same as the distance from the open end 17 of housing 11 to the shoulder 18 so that when the insert is fitted within bore 16, the lower end thereof is flush with the lower end of housing portion 13. An annular rib or snap looking projection 26 on the lower outer surface of insert 24 is received within an annular recess 27 in the lower end of housing portion 13 for snap locking the insert 24 in the bore 16. Alternatively, the insert may be ultrasonically sealed in the housing portion 13, if desired, rather than using the snap lock 26, 27. In order to prevent relative rotation between the insert 24 and housing portion 13, a plurality of axially extending ribs 28 on the lower outer surface of insert 24 are received within a plurality of mating recesses or grooves 29 in the lower inner surface of housing portion 13. An annular sealing ring 30 is fitted around the upper outer end of insert 24 to effect a fluid tight seal between the insert and housing. The upper end of insert 24 defines a flat, annular axially facing surface 31, substantially commensurate in size with the shoulder 18, and a screen type filter disc 32 is sealed to the surface 31 and extends across the bore 25 through insert 24.

The filter disc 32 includes a dome-shaped central portion 33 extending across the bore 25 and a flat, annular, marginal portion 34 overlying the surface 31. The flat marginal portion 34 is ultrasonically sealed to the surface 31 prior to insertion of the insert 24 into the bore 16 of housing 11. As seen in FIG. 2, the recess or chamber 19 provides space for receiving the dome-shaped portion 33 of filter disc 32 when the insert and filter are assembled to the housing 11, and the annular marginal portion 34 of the filter disc is tightly clamped or pressed between shoulder 18 and surface 31.

The housing 11 is preferably made of a plastic material such as polypropylene, and the filter disc is preferably a 10 micron nylon filter disc, although other suitable meshes and materials may be used. The insert 24 is made of a plastic material such as nylon or the like.

Referring to FIGS. 5 through 8, the method of assembling the adapter and filter is illustrated.

Figure 5:
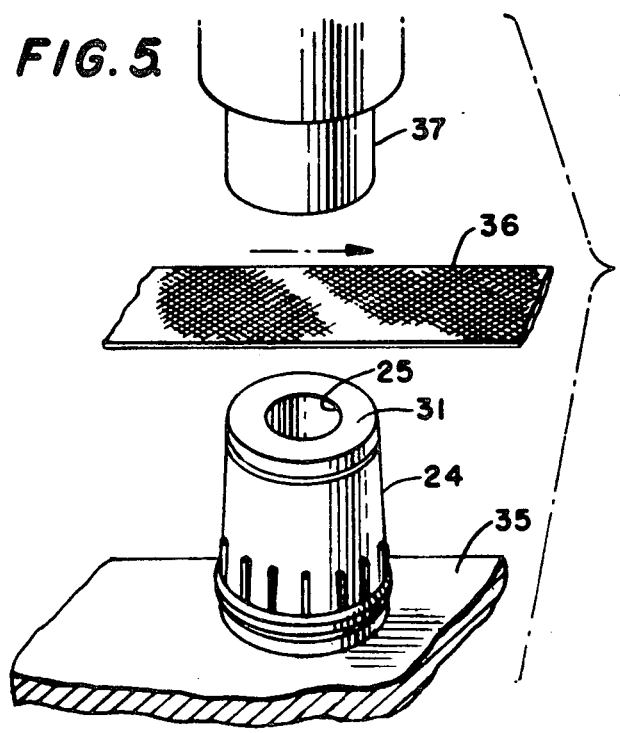
FIGS. 5 through 8 are illustrations of various steps used during the manufacture of the adapter and filter assembly.
Figure 6:
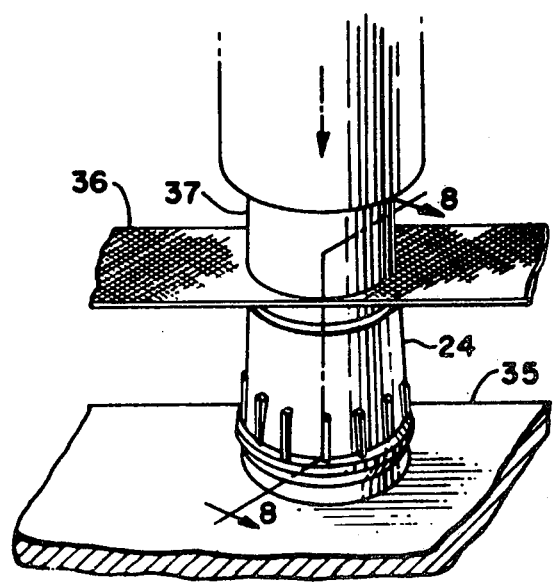
Figure 7:
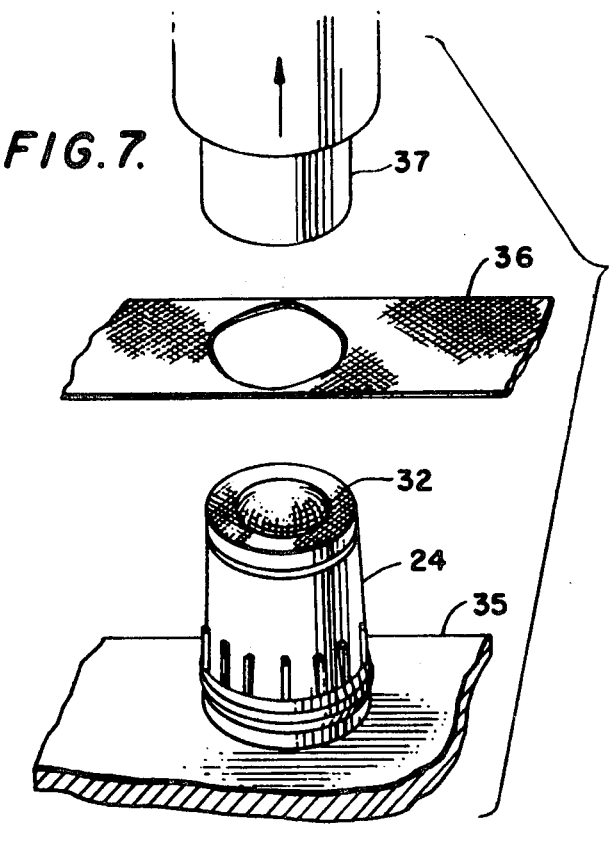

In FIG. 5, the insert 24 is positioned on a suitable support 35 and a web 36 of the filter material is positioned above the end surface 31 of the insert 24. A hot mandrel ultrasonic horn 37 is positioned above the web 36 of filter material in alignment with the insert 24, and FIG. 6, the mandrel or ultrasonic horn 37 is brought downwardly into engagement with the web 36 of filter material and the web 36 is held against the end surface 31 of the insert 24. In this step, the disc of filter material is simultaneously ultrasonically or otherwise suitably scaled to the surface 31 and cut from the web 36 of filter material, then, as seen in FIG. 7, the mandrel or ultrasonic horn 37 is retracted from engagement with the web 36 of filter material and the web 36 is withdrawn from the end of insert 24 leaving the disc 32 securely permanently affixed to the end of the insert. The web 36 is then advanced to bring a fresh portion of the web of filter material in alignment with the end of another insert 24 and the opertion is repeated.

Figure 8:
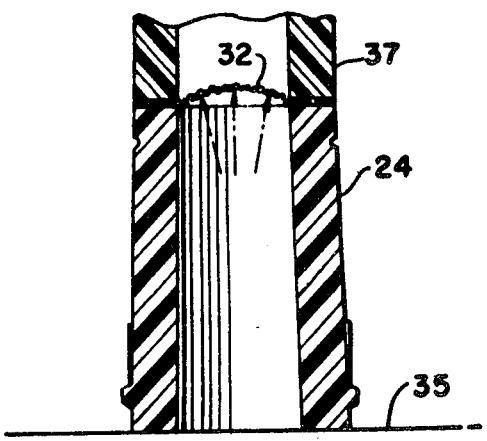

As seen in FIG. 8, the dome-shaped configuration of the filter disc is automatically obtained during the step of affixing the disc to the end of insert 24. It is believed that the dome-shaped configuration of the filter is obtained due in part to the pressure of air trapped beneath the filter material as the web and mandrel or ultrasonic horn are brought down into engagement with the end of insert 24, since this movement is quite rapid, and in part due to the temperature produced during the sealing and attachment of the disc of filter material to the end of insert 24.

Figure 4:
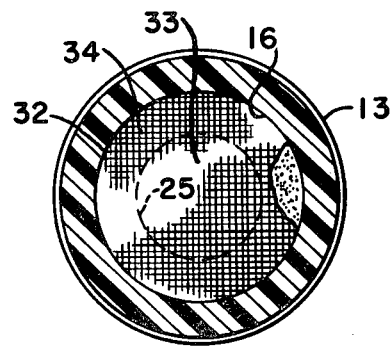
FIG. 4 is a sectional view taken along line 4—4 in FIG. 2.

As seen in FIG. 4a, the filter disc may be flat, as at 32', rather than dome shaped.

Although the hub or adapter 10 is described herein as including a needle or short section of PVC tubing adhesively bonded thereto, it could equally as well be provided with a Luer taper or other suitable construction for the attachment of a separate needle or tubing thereto.

Accordingly, a rugged and simple construction is quickly and economically obtained wherein the filter is automatically formed with a dome shape during the attachment thereof to the insert. After the filter disc is attached to the insert 24, the insert is fitted within the bore 16 of housing portion 13 and suitably affixed thereto as by means of the snap lock 26 or by an ultrasonic seal or other suitable means. The housing and insert may be manufactured according to conventional methods, such as by molding or the like.

In FIG. 9, an intravenous injection assembly or apparatus 38 includes a length of flexible IV tubing 39 connected at one end thereof to a drip chamber 40 of substantially conventional construction, and including a side wall 41 and a piercing tip 42 for piercing a bag or the like B to drain the contents therefrom. A chamber filter 43, made from nylon for example, and of 70 to 100 mesh, is secured within the drip chamber. A tubing adapter 44 has a pair of annular walls 45 and 46 defining a space therebetween in which one end of the drip chamber 40 is suitably secured, as by means of a sonic weld or adhesive or the like, and the tubing adapter 44 includes an axially extending central annular wall 47 projecting axially beyond the walls 45 and 46 into the drip chamber 40 and chamber filter 43, and a secondary chamber filter 48 is suitably secured to the end of wall 47, as by means of a sonic weld or the like. The tubing adapter 44 also includes an axially projecting, reduced diameter extension 49 inserted into the end of the length of IV tubing. A tubing adapter 50, preferably made of Latex rubber or the like, is secured to the other end of the length of IV tubing 39, and a filter tube 51, preferably made of clear polyvinyl chloride, has a male end 52 inserted within one end of the tubing adapter 50 and a female end 53. A needle adapter 54, preferably made of nylon or the like, has a reduced diameter male end 55 received in the female end 53 of filter tube 51, and has another male end 56 with a luer taper or the like for attachment thereto of a needle hub or other apparatus, as desired. As seen in FIG. 9, a needle hub 10, such as illustrated and described in FIGS. 1 through 8, is attached to the male end 56 of needle adapter 54. A guard, shown in phantom line at G, may be secured over the needle adapter 54 to maintain the adapter sterile until the time of use thereof, when the guard G may be removed and a hub or a needle or other apparatus attached thereto, as desired. A dome-shaped filter 57 is suitably secured to the end of portion 55 of the needle adapter 54 for filtering any contaminants from the fluid flowing through the IV tubing 39 and fittings 50 and 51. The filter 57 preferably is of a 5 or 10 micron size and comprises a final filter in the apparatus 38.

In addition to filtering contaminants from the liquid flowing through the intravenous injection assembly 38, the filters 43, 48 and 57 regulate the flow of liquid through the apparatus and maintain the rate of flows substantially at a predetermined constant flow rate during the time the liquid is being supplied from bag B, and notwithstanding the change in head or amount of liquid in the bag from the time at which the bag is full to the time it is empty. Moreover, when the hub 10 is affixed to the apparatus, an even further filter, 32, is available to remove any remaining contaminants from the fluid and to further aid in maintaining a constant flow rate.

If desired, clamp C of conventional construction may be provided on the length of IV tubing 39 to shut off flow therethrough or to set a desired rate of flow therethrough.

In FIG. 10, a slightly modified form of the invention is indicated at 38', ad is substantially identical to the form of the invention in FIG. 9, except that a filter 58 is secured in the IV tubing 39 between the ends thereof. The filter 58 may be secured at its periphery between adjacent end portions of the tubing, as shown, or a separate fitting may be secured in the length of tubing and the filter 58 suitably secured in the fitting. This filter 58 may be provided in lieu of either one of filters 43, 49 or 57, or in addition thereto. Also, a clamp C may be provided as in FIG. 9.

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

What is claimed is:

1. A needle adapter and filter therefor, comprising: a tubular housing having opposite ends and having a stepped axial bore therethrough defining an axially facing annular shoulder between the ends thereof; a tubular insert having opposite ends and having an axial bore therethrough and fitted coaxially within the bore through the housing, with the bore in the insert in axial alignment and registry with the bore in the housing, and one of said insert ends defining a flat, annular, surface normal to the axis of the insert, and substantially commensurate in size and shape with the shoulder; and a mesh filter having a generally dome-shaped central surface surrounded by a flat annular marginal section sealed and secured to said one end of the insert prior to positioning of the insert in the bore of the housing for assembly of the insert and filter as a unit within the housing, the flat annular section of said filter coinciding with said flat annular surface of the insert, said annular section of said filter sealed to said flat annular surface of said insert, and said annular section of said filter further clamped between the insert end surface and the shoulder, thereby defining a relatively large annular seal area to effect a leakproof structure, whereby the filter filters contaminants or particulate matter from materials or solutions flowing through said adapter.

2. A needle adapter and filter as in claim 1 wherein said filter is ultrasonically sealed to said end surface of said insert.

3. A needle adapter and filter as in claim 1, wherein said filter is cemented to said end surface of said insert.

4. A needle adapter and filter as in claim 1, wherein a cavity is in said housing adjacent said shoulder, and said dome shaped filter projects into said cavity.

5. A needle adapter and filter as in claim 1, wherein said bore through said housing is outwardly tapered at one end thereof to define a frusto-conically shaped cavity in one end of said housing, hollow tubular means fixed in said bore and extending through said cavity, and an epoxy adhesive filling said cavity and bonding said tubular means to said housing.

6. A needle adapter and filter as in claim 5, wherein said insert has a plurality of axially extending ribs thereon, and said housing has a plurality of axially extending grooves in said bore, said ribs on said insert received in said grooves to prevent relative rotation between the insert and housing.

* * * * *